United States Patent [19]

Nakajima et al.

[11] Patent Number: 4,831,162

[45] Date of Patent: May 16, 1989

[54] PREPARATION PROCESS OF ETHYLENE OXIDE

[75] Inventors: Mutsuo Nakajima; Hisaharu Kuboyama; Tadashi Komiyama, all of Yokohama; Hiroshi Kimura, Kamakura; Kenji Yoshida, Fujisawa, all of Japan

[73] Assignee: Mitsui Toatsu Chemicals, Incorporated, Tokyo, Japan

[21] Appl. No.: 15,519

[22] Filed: Feb. 13, 1987

Related U.S. Application Data

[63] Continuation of Ser. No. 747,192, Jun. 20, 1985, abandoned.

[30] Foreign Application Priority Data

Jun. 25, 1984 [JP] Japan ................. 59-129229

[51] Int. Cl.$^4$ ........................... C07D 301/10
[52] U.S. Cl. ................................ 549/534
[58] Field of Search ........................ 549/534

[56] References Cited

U.S. PATENT DOCUMENTS

| | | | |
|---|---|---|---|
| 2,279,469 | 4/1942 | Law et al. | 549/534 |
| 2,279,470 | 4/1942 | Law et al. | 549/534 |
| 2,479,884 | 6/1949 | West et al. | 549/534 |
| 2,963,444 | 12/1960 | Nixon | 502/50 |
| 4,007,135 | 2/1977 | Hayden et al. | 549/534 |
| 4,012,425 | 3/1977 | Nielsen et al. | 549/534 |
| 4,051,068 | 9/1977 | Rebsdat et al. | 549/534 |
| 4,206,128 | 6/1980 | Cavitt | 549/534 |
| 4,212,772 | 7/1980 | Mross et al. | 549/534 |
| 4,335,014 | 6/1982 | Alfranseder et al. | 549/534 |
| 4,419,276 | 12/1983 | Bhasin et al. | 549/534 |
| 4,425,439 | 1/1984 | Busse | 549/534 |
| 4,478,948 | 10/1984 | Rebsdat et al. | 549/534 |

FOREIGN PATENT DOCUMENTS

| | | |
|---|---|---|
| 3642 | 8/1979 | European Pat. Off. |
| 1413251 | 11/1975 | United Kingdom |
| 1515514 | 6/1978 | United Kingdom |
| 2043481A | 10/1980 | United Kingdom |

OTHER PUBLICATIONS

English translation of French patent No. 1,138,941, 02/04/57.

Primary Examiner—Richard L. Raymond
Assistant Examiner—Mark W. Russell
Attorney, Agent, or Firm—Flynn, Thiel, Boutell & Tanis

[57] ABSTRACT

Ethylene is oxidized into ethylene oxide by bringing a feed gas mixture, which contains the ethylene, oxygen and at least 1 vol. % of carbon dioxide as well as at least 0.5 vol. ppm of a chlorine-containing burning reaction decelerator and at least 1 vol. ppm as calculated in terms of nitrogen monoxide of a nitrogen oxide and/or a precursor thereof, into contact with a catalyst which carries silver and as a practically sole alkali metal, rubidium at an Rb/Ag atomic ratio of 2/1000–7/1000 on a fire-resistant carrier having a specific surface area of 1 m$^2$/g or smaller.

13 Claims, No Drawings

PREPARATION PROCESS OF ETHYLENE OXIDE

BACKGROUND OF THE INVENTION

This application is a continuation of U.S. Ser. No. 747,192, filed June 20, 1985, now abandoned.

(a) Field of the Invention

This invention relates to a process for preparing ethylene oxide by vapor-phase catalytic oxidation of ethylene with molecular oxygen, and more specifically to a process for preparing ethylene oxide stably and with a high yield for a long period of time by using a feed gas which contains at least 1 vol. % of $CO_2$, a nitrogen oxide and/or a precursor thereof, and a chlorine-containing reaction modifier (a chlorine-containing burning reaction decelerator).

(b) Description of the Prior Art

As industrial processes for preparing ethylene oxide by subjecting ethylene to vapor-phase catalytic oxidation with molecular oxygen, there have been known "the air process" employing air and "the oxygen process" making use of oxygen of high purity, both, as sources for the molecular oxygen. In each of these processes, mild reaction conditions are employed to improve the yield of resulting ethylene oxide and at the same time to minimize the byproduction of $CO_2$ as much as possible. For this reason, ethylene and oxygen which have been fed to a reactor are converted only partly. In order to facilitate the reutilization of expensive raw materials such as ethylene and the like, many plants are thus operated in accordance with the recirculation method in which ethylene oxide is separated from a gaseous reaction mixture discharged from each reactor and after partial removal of $CO_2$, the majority of the remaining gas is returned to the reactor. The $CO_2$ removal is usually effected by causing the gaseous reaction mixture to pass through an aqueous alkaline solution. It is however uneconomical to remove $CO_2$ in its entirety, because such an attempt requires not only huge facilities but also tremendous operation costs. For these reasons, feed gases usually contain at least 1 vol. % of $CO_2$ in plants operated for ordinary industrial production.

In addition, chlorine compounds are usually contained at trace levels in such feed gases. Although these chlorine componds impair catalytic activities, they have greater deceleration effects against the $CO_2$-yielding reaction than against the ethylene oxide forming reaction. Consequently, they serve to improve the conversion of reacted ethylene into ethylene oxide (the selectivity coefficient for ethylene oxide).

Much research has heretofore been carried out with a view toward developing catalysts which feature high activities, high selectivity coefficients for ethylene oxide and long service life when used in combination with feed gases containing such components as mentioned above. As the result of such research, there have been proposed a number of catalysts formed basically of silver-bearing catalysts and added further with trace amounts of reaction accelerators, notably, alkali metals. For example, Japanese Patent Laid-open No. 30286/1974 discloses that good results can be brought about from the use of a catalyst prepared by causing 0.00035–0.0030 gram equivalent (by weight) per kg of the resultant catalyst of potassium, rubidium and/or cesium to deposit simultaneously with silver on a porous catalyst. Catalysts prepared by such a method lead certainly to improved selectivity coefficients for ethylene oxide than those prepared without alkali metals. However, as apparent from Example VI of the above laid-open patent specification, the highest selectivity coefficient for ethylene oxide can be obtained at Rb/Ag=2.91/1000(by atomic ratio) when Rb is incorporated (see, Catalyst R in Table III of the above laid-open specification). However, the selectivity coefficient for ethylene oxide and catalytic activities are both reduced as the proportion of Rb increases from the above level. Eventually, Rb may become even harmful. Even the highest selectivity coefficient for ethylene oxide which was achieved by the addition of Rb was still as low as 80%, which can hardly be considered to be sufficient.

Japanese Patent Laid-open No. 1191/1978 also discloses to the effect that good results can be obtained by a silver catalyst which contains 0.1–2 atomic percent of sodium along with 0.05–0.35 atomic percent of potassium, 0.003–0.25 atomic percent of rubidium or 0.0005–0.2 atomic percent of cesium or a mixture of two or more of these heavy alkali metals, all based on the silver. Furthermore, it is disclosed in Japanese Patent Laid-open No. 127144/1980 that good results can be brought about by carrier-base catalysts each of which contains, in combination, (a) cesium and (b) at least one alkali metal other than cesium, selected from the group consisting of lithium, sodium, potassium and rubidium. Although these catalysts have higher activities and higher selectivity than those carrying only silver thereon, their selectivity coefficients for ethylene oxide are still as low as 82% and are hence not considered to be sufficient.

In this respect, it is worthwhile to pay attention to Japanese Patent Laid-open No. 90591/1975 because some of the carrier-base catalysts disclosed therein, which were each composed of sodium, cesium, rubidium and/or potassium; magnesium, strontium, calcium and/or preferably barium; and silver, gave selectivity coefficients for ethylene oxide higher than 90%. These catalysts feature higher alkali metal contents than those known before that time. The activities of these catalysts are however so low that they can hardly be said to be practical. Notwithstanding the passage "the selectivity efficient for the reaction can be increased by using carbon dioxide" which appears on page 7, lower left column, line 2 from the bottom of the above-mentioned laid-open patent specification, all the examples of the laid-open patent specification were, as a matter of fact, conducted with feed gases which did not contain carbon dioxide. According to the present inventors' experiences, carbon dioxide contained in feed gases acts on such catalysts of high alkali metal contents in such a way that it would rather lower not only their selectivity for ethylene oxide but also their activities. Therefore, such catalysts must be said to be still less suitable for industrial production.

Japanese Patent Laid-open No. 115306/1979 discloses a process for preparing ethylene oxide by bringing ethylene into contact with oxygen in the presence of a silver-containing catalyst and a chlorine-containing reaction regulator, which comprises bringing the catalyst into simultaneous contact with a nitrate or a nitrite-yielding material present in a vapor phase so that the selectivity coefficient of the catalyst is either improved or at least allowed either to retain or to restore a part of its catalytic ability.

The above preparation process may certainly be effective for improving the selectivity factors of such catalysts for ethylene oxide or for retaining parts of their catalytic abilities in certain instances, namely, when no carbon dioxide is contained in feed gases as employed in the examples of the laid-open patent specifications. It is however difficult to maintain the activities and selectivity coefficients of such catalysts at sufficiently high levels when carbon dioxide is contained at certain levels in feed gases. The activities of catalysts are lowered too much to make the process practical, especially, when the alkali metal contents are high as seen in the examples of the above-mentioned laid-open patent specification (notably, where Na and/or K contents are high) and carriers having high specific surface areas in excess of 0.5 $m^2/g$ are employed.

As has been mentioned above, there has not yet been developed any preparation process in which a catalyst has high selectivity and exhibits high activities stably under usual industrial production conditions, namely, for a feed gas with carbon dioxide contained therein in advance.

SUMMARY OF THE INVENTION

An object of this invention is to provide an industrially-improved preparation process of ethylene oxide, which employs a feed gas containing ethylene and oxygen along with at least 1 vol. % of carbon dioxide.

Another object of this invention is to provide a preparation process of ethylene oxide, which makes use of a catalyst capable of showing high activities and high selectivity stably for a feed gas with at least 1 vol. % of carbon dioxide contained therein.

The present inventors have found that the above objects can be achieved, even with feed gases containing carbon dioxide, by specifying the type and amount of an alkali metal added to silver and the specific surface area of a catalyst carrier adapted to carry the silver and alkali metal and also incorporating a specific amount of a specific additive in a feed gas.

The preparation process of ethylene oxide according to this invention comprises bringing a feed gas mixture, which contains ethylene, oxygen and at least 1 vol. % of carbon dioxide as well as at least 0.5 vol. ppm of a chlorine-containing burning reaction decelerator and at least 1 vol. ppm as calculated in terms of nitrogen monoxide of a nitrogen oxide and/or nitrogen oxide precursor, into contact with a silverbearing catalyst containing silver and as a practically sole alkali metal, rubidium on a porous fire-resistant carrier having a specific surface area of 1 $m^2/g$ or smaller, the atomic ratio of said rubidium to said silver (Rb/Ag) being 2/1000-7/1000, so as to oxidize the ethylene in the feed gas mixture with molecular oxygen.

DETAILED DESCRIPTION OF THE INVENTION

Conventional carriers employed for the preparation of ethylene oxide are all suited as porous fire-resistant carriers useful in the practice of this invention. As examples of such carriers, may be mentioned alumina, silica, magnesia, zirconia, silicon carbide, diatomaceous earth, etc. Carriers containing alumina and/or silica are preferred, with carriers of high α-alumina content being particularly preferred. Among properties of these carriers, their specific surface areas are especially important. If this specific suface area should be excessively large, the selectivity of the catalyst for ethylene oxide will be lowered and its service life will also be shortened. If it is too small on the other hand, the activities of the catalyst will be lowered. Whichever the case, the process will become economically disadvantageous. The specific surface area of the carrier may be 1 $m^2/g$ or smaller, preferably 0.05-1 $m^2/g$, more preferably 0.07-0.7 $m^2/g$, or most preferably 0.1-0.5 $m^2/g$. The apparent porosity of the carrier may preferably be 40-60 vol. %, or notably 45-50 vol. %. The pore volume may preferably be 0.1-0.5 cc/g, or notably 0.2-0.3 cc/g. The average pore diameter may preferably be 1-12 micrometers, or notably 1.5-10 micrometers. It is preferred to use a carrier having pore diameters at least 70% of which range from 1.5 to 15 micrometers.

In order to obtain a catalyst useful in the practice of this invention, a variety of methods may be employed as methods for causing a carrier to bear silver thereon. For example, the catalyst may be obtained by immersing the carrier in an aqueous solution of silver nitrate, draining the aqueous solution, drying the carrier, and finally subjecting the thus-treated carrier to a reduction treatment with hydrogen. Alternatively, the carrier may be immersed in an ammonia-containing aqueous solution of silver oxalate or silver carbonate and after drainage of the aqueous solution, heated, thereby subjecting the ammonia complex of silver oxalate or silver carbonate to pyrolysis and thus causing the carrier to bear the resultant silver metal thereon. As a further alternative method, the carrier may be impregnated with an aqueous solution of a silver salt and a combined mixture of one or more nitrogen-containing compounds, followed by a heat treatment of the impregnated carrier in the same manner as mentioned above. As exemplary silver salts, there may be mentioned inorganic silver salts such as silver nitrate, silver nitrite and silver carbonate, and silver carboxylates such as silver oxalate, silver acetate, silver lactate and silver succinate. Illustrative of such nitrogen-containing compounds are ammonia, aliphatic monoamines, alkylene diamines, alkanolamines, aminoethers, etc. Two or more of these silver salts may be used in combination. Similarly, two or more of such nitrogen-containing compounds may be employed in combination. It is possible, for example, to use the solutions proposed by the present inventors in Japanese Patent Application No. 197656/1983, each of which contains a silver salt, monoamine and amino-substituted ether.

The silver content of each catalyst useful in the practice of this invention may be 3 wt. % or higher, preferably 3-20 wt. %, or most preferably 5-12 wt. %. If the silver content should be too low, no good results can be expected. Even if it should be increased to an excessively high level on the other hand, no significant additional improvement can be expected with respect to the performance of the resulting catalyst. Conversely, the economical loss due to the use of expensive silver in such a large amount will be far greater.

The catalyst to be used in the present invention must contain rubidium as a practically sole alkali metal. If the alkali metal should be cesium, the selectivity coefficient for ethylene oxide will be unacceptably low. If it should be sodium or potassium on the other hand, a high selectivity coefficient may be exhibited only tentatively. When such a catalyst is used in a feed gas mixture containing $CO_2$ at a certain level, its catalytic performance will not be stable and its service life will be short. Therefore, such a catalyst is not suited for use in such a feed gas mixture. Further, no additional effects will be observed where the alkali metal is lithium. Different from such catalysts, a rubidium-containing catalyst can show a high selectivity coefficient stably for a long period of time even in the presence of $CO_2$ provided that a nitrogen oxide and/or nitrogen oxide precursor are contained at suitable levels in a feed gas mixture. It should however be borne in mind that the rubidium content is critical and must thus be controlled to give 2-7 gram atoms, preferably 2.5-6.5 gram atoms, or most preferably 3-6 gram atoms, each per 1000 gram atoms of silver. If the rubidium content should be too low, both activities and selectivity will be low. If it should be increased too much, the resulting catalysts are usually unstable and shortened in service life although the selectivity coefficients of some of such catalysts may be increased tentatively. As rubidium compounds usable upon preparation of catalysts, conventionally-known rubidium compounds may all be used effectively. As such compounds, may be mentioned by way of example inorganic salts such as rubidium nitrate, rubidium nitrite, rubidium carbonate, rubidium bicarbonate, rubidium sulfate, rubidium chloride, rubidium fluoride, rubidium chlorate, rubidium chlorite, rubidium hypochlorite, rubidium phosphate and rubidium pyrophosphate; and rubidium hydroxide. In addition, carboxylates such as rubidium acetate, rubidium formate, rubidium oxalate, rubidium malonate and rubidium succinate are also effective. These rubidium compounds may be deposited on carriers either simultaneously with or before or after the deposition of silver on the same carriers.

Another characteristic feature of this invention resides in the composition of each feed gas mixture. In the feed gas, a nitrogen oxide and/or nitrogen oxide precursor must be contained in addition to its routinely-known components. Unless such additional compounds are contained in the feed gas, the stability of the performance of the catalyst will be significantly lowered and its activities and selectivity will both be reduced extremely in a relatively short period of time although the selectivity coefficient of the catalyst for ethylene oxide may tentatively be increased by a slight degree compared with that available when the additional compounds are contained. It is necessary to control the total content of such a nitrogen oxide and/or nitrogen oxide precursor at a level of at least 1 vol. ppm, preferably within the range of 2-500 vol. ppm, or most preferably within the range of 3-200 vol. ppm, all as calculated in terms of nitrogen monoxide. As examples of such a nitrogen oxide, may be mentioned $NO$, $NO_2$, $N_2O_4$, $N_2O_5$, $N_2O_3$, etc. As illustrative of such a nitrogen oxide precursor, may be mentioned aliphatic monoamines such as methylamine, ethylamine, n-propylamine and iso-propylamine, alkanolamines such as ethanolamine, aliphatic diamines such as ethylenediamine, and ammonia. By the way, the abovementioned "as calculated in terms of nitrogen monoxide" means the maximum amount of nitrogen monoxide to be obtained by either oxidizing or reducing the corresponding nitrogen oxide and/or nitrogen oxide precursor.

It is essential that each feed gas mixture also contains a chlorine-containing compound as a burning reaction decelerator, because the catalyst is imparted with high selectivity for the first time when this chlorine-containing compound is caused to exist. Illustrative of such a chlorine-containing compound may include chlorine-substituted derivatives of aliphatic hydrocarbons, such as vinyl chloride, ethylene dichloride and methyl chloride, and chlorine-substituted derivatives of aromatic hydrocarbons such as chlorobenzene and diphenyl chloride. Appropriate results will be brought about when such a chlorine-containing burning reaction decelerator is contained in an amount of at least 0.5 vol. ppm, preferably 0.7-100 vol. ppm, or most preferably 1.0-50 vol. ppm in the feed gas.

The feed gas mixture also contains carbon dioxide. The carbon dioxide content in the feed gas is at least 1 vol. %, usually 1-20 vol. %, or preferably 1-10 vol. %.

Such a $CO_2$-containing feed gas may include the feed gas which is recovered in a preparation proces of ethylene and contains byproduced carbon dioxide.

In the present invention, the reaction temperature may be 150°-300° C. or preferably 180°-270° C., the reaction pressure 0-50 kg/cm$^2$G or preferably 0-30 kg/cm$^2$G, the space velocity 100-10000 hr$^{-1}$ or preferably 150-7000 hr$^{-1}$. The feed gas contains, beside the above-mentioned nitrogen oxide and/or nitrogen oxide precursor and the chlorine containing burning reaction decelerator, at least 1 vol. % of $CO_2$ and usually, 0.5-50 vol. % of ethylene, 3-20 vol. % of oxygen and the remainder of lower hydrocarbons such as methane and ethane and inert gases such as nitrogen and argon.

This invention will hereinafter be describe more specifically by the following Examples and Comparative Examples.

EXAMPLE 1

Catalyst No. 1 was prepared in the following manner.

Dissolved in 18.63 g of water were 15.01 g of isopropylamine and 4.75 g of morpholine, followed by further dissolution of 18.50 g of silver nitrate and 0.067 g of rubidium nitrate in the resultant solution to prepare a dipping solution. Forty grams of a carrier, which had a specific surface area of 0.30 m$^2$/g, apparent porosity of 56% and pores, 81% of said pores ranging from 1 to 30 micrometers, and contained 93% of $Al_2O_3$, were immersed. The carrier with the dipping solution contained therein was dried at 145° C. for 3 hours followed by its firing at 160° C. for 2 hours and at 260° C. for further 3 hours in air.

As a result of analysis, the thus-obtained Catalyst No. 1 contained 8.3% of silver with Rb/Ag=4.2/1000 (by atomic ratio).

Using Catalyst No. 1, a reaction was conducted under such conditions as given below.

Thirty grams of Catalyst No. 1 were packed in a glass-made tubular reactor having an internal diameter of 17 mm, to which was supplied at a velocity of 6 liters per hour a feed gas which consisted of 21.1 vol. % of ethylene, 6.2 vol. % of oxygen, 5.3 vol. % of carbon dioxide, 4.8 vol. ppm of vinyl chloride, 9.8 vol. ppm of nitrogen monoxide and the remainder of nitrogen. The reaction was carried out at 230° C. for 1 week and then at a raised temperature of 250° C. for further 1 week.

Results are given in Table 1.

COMPARATIVE EXAMPLE 1

Catalyst No. 2 was obtained in exactly the same manner as in Example 1. With Catalyst No. 2, a reaction was conducted in exactly the same manner as in Example 1 except that among the components of the feed gas of Example 1, nitrogen monoxide was excluded. Results are shown in Table 1.

COMPARATIVE EXAMPLE 2

In exactly the same manner as in Example 1, Catalyst No. 3 was obtained. Using Catalyst No. 3, a reaction was conducted in exactly the same manner as in Example 1 except that among the components of the feed gas of Example 1, vinyl chloride was excluded. Results are shown in Table 1.

As apparent from Example 1 and Comparative Examples 1 and 2, the activities and selectivity of a catalyst can be stably maintained at high levels for the first time when a nitrogen oxide and/or nitrogen oxide precursor and a chlorine-containing burning reaction decelerator are caused to exist in a feed gas.

TABLE 1

| Catalyst No. | Ex. 1 1 | Comp. Ex. 1 2 | Comp. Ex. 2 3 |
|---|---|---|---|
| Catalyst composition: | | | |
| Silver content (wt. %) | 8.3 | 8.3 | 8.3 |
| Rb/Ag (by atomic ratio) | 4.2/1000 | 4.2/1000 | 4.2/1000 |
| Feed gas composition: | | | |
| Ethylene (vol. %) | 21.1 | 21.1 | 21.1 |
| Oxygen (vol. %) | 6.2 | 6.2 | 6.2 |
| $CO_2$ (vol. %) | 5.3 | 5.3 | 5.3 |
| NO (vol. ppm) | 9.8 | 0 | 9.8 |
| Vinyl chloride (vol. ppm) | 4.8 | 4.8 | 0 |
| Nitrogen | balance | balance | balance |
| 1 Week after at 230° C.: | | | |
| Conversion of ethylene (%) | 8.0 | 1.8 | 4.9 |
| Selectivity coefficient for ethylene oxide (%) | 89.4 | 69.7 | 68.1 |
| 1 Week after at 250° C.: | | | |
| Conversion of ethylene (%) | 12.8 | 0.6 | 3.5 |
| Selectivity coefficient for ethylene oxide (%) | 87.0 | 63.2 | 61.2 |
| Remarks | stable | gradual activity drop | gradual activity drop |

COMPARATIVE EXAMPLE 3

Catalyst No. 4 was obtained in exactly the same manner as in Example 1 except that sodium nitrate was used in place of rubidium nitrate. As a result of analysis, Catalyst No. 4 contained 8.3 wt. % of silver with Na/Ag=4.2/1000 (by atomic ratio).

Using Catalyst No. 4, a reaction was conducted in exactly the same manner as in Example 1. Results are given in Table 2.

COMPARATIVE EXAMPLE 4

Catalyst No. 5 was obtained in exactly the same manner as in Example 1 except that potassium nitrate was used in place of rubidium nitrate. As a result of analysis, Catalyst No. 5 contained 8.3 wt. % of silver with K/Ag=4.2/1000 (by atomic ratio).

Using Catalyst No. 5, a reaction was conducted in exactly the same manner as in Example 1. Results are given in Table 2.

COMPARATIVE EXAMPLE 5

Catalyst No. 6 was obtained in exactly the same manner as in Example 1 except that cesium nitrate was used in place of rubidium nitrate. As a result of analysis, Catalyst No. 6 contained 8.3 wt. % of silver with Cs/Ag=4.2/1000 (by atomic ratio).

Using Catalyst No. 6, a reaction was conducted in exactly the same manner as in Example 1. Results are given in Table 2.

TABLE 2

| Catalyst No. | Comp. Ex. 3 4 | Comp. Ex. 4 5 | Comp. Ex. 5 6 |
|---|---|---|---|
| Type of added alkali metal | $NaNO_3$ | $KNO_3$ | $CsNO_3$ |
| Catalyst composition: | | | |
| Silver content (wt. %) | 8.3 | 8.3 | 8.3 |
| Me*/Ag (by atomic ratio) | 4.2/1000 | 4.2/1000 | 4.2/1000 |
| Feed gas composition: | | | |
| Ethylene (vol. %) | 21.1 | 21.1 | 21.1 |
| Oxygen (vol. %) | 6.2 | 6.2 | 6.2 |
| $CO_2$ (vol. %) | 5.3 | 5.3 | 5.3 |
| NO (vol. ppm) | 9.8 | 9.8 | 9.8 |
| Vinyl chloride (vol. ppm) | 4.8 | 4.8 | 4.8 |
| Nitrogen | balance | balance | balance |
| 1 Week after at 230° C.: | | | |
| Conversion of ethylene (%) | 4.8 | 7.7 | <1 |
| Selectivity coefficient for ethylene oxide (%) | 78.6 | 86.9 | <65 |
| 1 Week after at 250° C.: | | | |
| Conversion of ethylene (%) | 10.2 | 7.3 | <1 |
| Selectivity coefficient for ethylene oxide (%) | 75.2 | 75.8 | <65 |
| Remarks | stable | gradual activity drop | un-** stable |

*Me means an alkali metal.
**The conversion of ethylene was less than 1% and the selectivity coefficient for ethylene oxide was less than 65%. Due to undue variations, no reliable data were obtained.

COMPARATIVE EXAMPLE 6

Catalyst Nos. 7, 8 and 9 were prepared in exactly the same manner as in Example 1 except that sodium nitrate, potassium nitrate and cesium nitrate were respectively added, to a level different from rubidium nitrate in Example 1, in place of rubidium nitrate and the amounts of water used, isopropylamine, morpholine, silver nitrate and carrier were doubled.

As the result of analysis, Catalyst No. 7 was found to contain 8.3 wt. % of silver with Na/Ag=18/1000 (by atomic ratio). Catalyst No. 8 contained 8.3 wt. % of silver with K/Ag=6/1000 (by atomic ratio). Further, Catalyst No. 9 contained 8.3 wt. % of silver with Cs/Ag=2.2/1000 (by atomic ratio).

(First experiment)

Thirty gram portions of Catalyst Nos. 7, 8 and 9 were respectively packed in glass-made tubular reactors having an internal diameter of 17 mm, to which were respectively supplied at a velocity of 6 liters per hour a feed gas which consisted of 20.1 vol. % of ethylene, 6.1 vol. % of oxygen, 9.9 vol. ppm of nitrogen monoxide, 4.9 vol. ppm of vinyl chloride and the remainder of nitrogen. Reactions were carried out at 230° C. for 4 days. Results are summarized in Table 3.

(Second experiment)

Then, 30 gram fresh portions of Catalyst Nos. 7, 8 and 9 were packed and reactions were carried out in exactly the same manner as in Example 1 except that the composition of the feed gas was somewhat changed. Results are given also in Table 3.

TABLE 3

| | Comparative Example 6 | | |
|---|---|---|---|
| Catalyst No. | 7 | 8 | 9 |
| Type of added alkali metal | $NaNO_3$ | $KNO_3$ | $CsNO_3$ |
| Catalyst composition: | | | |
| Silver content (wt. %) | 8.3 | 8.3 | 8.3 |
| Me*/Ag (by atomic ratio) | 18/1000 | 6/1000 | 2.2/1000 |
| First Experiment | | | |
| Feed gas composition: | | | |

TABLE 3-continued

|  | Comparative Example 6 | | |
|---|---|---|---|
| Catalyst No. | 7 | 8 | 9 |
| Ethylene (vol. %) | 20.1 | 20.1 | 20.1 |
| Oxygen (vol. %) | 6.1 | 6.1 | 6.1 |
| NO (vol. ppm) | 9.9 | 9.9 | 9.9 |
| Vinyl chloride (vol. ppm) | 4.9 | 4.9 | 4.9 |
| Nitrogen | balance | balance | balance |
| Performance after 4 days at 230° C.: | | | |
| Conversion of ethylene (%) | 7.0 | 10.3 | 8.6 |
| Selectivity coefficient for ethylene oxide (%) | 91.5 | 92.1 | 83.7 |
| Second Experiment | | | |
| Feed gas composition: | | | |
| Ethylene (vol. %) | 21.3 | 21.3 | 21.3 |
| Oxygen (vol. %) | 6.2 | 6.2 | 6.2 |
| $CO_2$ (vol. %) | 4.9 | 4.9 | 4.9 |
| NO (vol. ppm) | 10.1 | 10.1 | 10.1 |
| Vinyl chloride (vol. ppm) | 4.7 | 4.7 | 4.7 |
| Nitrogen | balance | balance | balance |
| Performance after 1 week at 230° C.: | | | |
| Conversion of ethylene (%) | 4.3 | 6.7 | 6.9 |
| Selectivity coefficient for ethylene oxide (%) | 87.2 | 88.3 | 81.9 |
| Performance after 1 week after at 250° C.: | | | |
| Conversion of ethylene (%) | 3.9 | 6.1 | 13.7 |
| Selectivity coefficient for ethylene oxide (%) | 80.6 | 82.5 | 78.3 |
| Remarks | gradual activity drop | gradual activity drop | stable |

*Me means an alkali metal.

EXAMPLES 2-6 AND COMPARATIVE EXAMPLE 7

In exactly the same manner as in Example 1 except that rubidium nitrate was added respectively in different amounts, Catalyst Nos. 10, 11, 12, 13, 14 and 15 were prepared. Reactions were carried out using these catalysts in exactly the same manner as in Example 1 except that the reactions were not effected at 250° C. Results are summarized in Table 4.

TABLE 4

| Catalyst No. | Ex. 2 10 | Ex. 3 11 | Ex. 4 12 |
|---|---|---|---|
| Catalyst composition: | | | |
| Silver content (wt. %) | 8.3 | 8.3 | 8.3 |
| Rb/Ag (by atomic ratio) | 3.5/1000 | 3.9/1000 | 4.1/1000 |
| Feed gas composition: | | | |
| Ethylene (vol. %) | 21.1 | 21.1 | 21.1 |
| Oxygen (vol. %) | 6.2 | 6.2 | 6.2 |
| $CO_2$ (vol. %) | 5.2 | 5.2 | 5.2 |
| NO (vol. ppm) | 9.8 | 9.8 | 9.8 |
| Vinyl chloride (vol. ppm) | 4.8 | 4.8 | 4.8 |
| Nitrogen | balance | balance | balance |
| 1 Week after at 230° C.: | | | |
| Conversion of ethylene (%) | 12.6 | 9.2 | 9.0 |
| Selectivity coefficient for ethylene oxide (%) | 84.2 | 87.6 | 88.7 |
| Remarks | stable | stable | stable |

| Catalyst No. | Ex. 5 13 | Ex. 6 14 | Comp. Ex. 7 15 |
|---|---|---|---|
| Catalyst composition: | | | |
| Silver content (wt. %) | 8.3 | 8.3 | 8.3 |
| Rb/Ag (by atomic ratio) | 4.3/1000 | 4.5/1000 | 10.0/1000 |
| Feed gas composition: | | | |
| Ethylene (vol. %) | 21.1 | 21.1 | 21.1 |
| Oxygen (vol. %) | 6.2 | 6.2 | 6.2 |
| $CO_2$ (vol. %) | 5.2 | 5.2 | 5.2 |
| NO (vol. ppm) | 9.8 | 9.8 | 9.8 |
| Vinyl chloride (vol. ppm) | 4.8 | 4.8 | 4.8 |
| Nitrogen | balance | balance | balance |
| 1 Week after at 230° C.: | | | |
| Conversion of ethylene (%) | 9.2 | 8.0 | 1.1 |
| Selectivity coefficient for ethylene oxide (%) | 88.8 | 89.2 | 93.1 |
| Remarks | stable | stable | gradual activity drop |

EXAMPLES 7-13 AND COMPARATIVE EXAMPLES 8 & 9

Catalyst Nos. 16-24 were each prepared in the following manner.

Dissolved in 11.72 g of water were 18.01 g of isopropylamine and 5.70 g of morpholine, followed by further addition and thorough dissolution of 22.20 g of silver nitrate and rubidium nitrate in the resultant solution. Forty grams of a carrier, which had a specific surface area of 0.25 m²/g, apparent porosity of 45% and pores, 97% of said pores ranging from 1 to 30 micrometers, and contained about 99.3% of $Al_2O_3$, were immersed. The carrier with the dipping solution contained therein was dried at 145° C. for 3 hours, followed by its firing at 160° C. for 2 hours and at 260° C. for further 3 hours in air. The silver contents and atomic Rb/Ag ratios of the thus-obtained catalysts, Catalyst Nos. 16-24, are given in Table 5.

Using these catalysts, reactions were conducted in the same manner as in Example 1 except that the composition of the feed gas was somewhat different and no reactions were effected at 250° C. The composition of the feed gas and reaction results are summarized in Table 5.

TABLE 5

| Catalyst No. | Ex. 7 16 | Ex. 8 17 | Ex. 9 18 |
|---|---|---|---|
| Catalyst composition: | | | |
| Silver content (wt. %) | 7.2 | 7.2 | 7.2 |
| Rb/Ag (by atomic ratio) | 2.5/1000 | 3.0/1000 | 3.5/1000 |
| Feed gas composition: | | | |
| Ethylene (vol. %) | 20.5 | 20.5 | 20.5 |
| Oxygen (vol. %) | 6.1 | 6.1 | 6.1 |
| $CO_2$ (vol. %) | 5.0 | 5.0 | 5.0 |
| NO (vol. ppm) | 10.1 | 10.1 | 10.1 |
| Vinyl chloride (vol. ppm) | 4.7 | 4.7 | 4.7 |
| Nitrogen | balance | balance | balance |
| 1 Week after at 230° C.: | | | |
| Conversion of ethylene (%) | 6.3 | 7.1 | 8.2 |
| Selectivity coefficient for ethylene oxide (%) | 81.6 | 83.0 | 85.0 |
| Remarks | stable | stable | stable |

| Catalyst No. | Ex. 10 19 | Ex. 11 20 | Ex. 12 21 |
|---|---|---|---|
| Catalyst composition: | | | |
| Silver content (wt. %) | 7.2 | 7.2 | 7.2 |
| Rb/Ag (by atomic ratio) | 3.8/1000 | 4.0/1000 | 5.0/1000 |
| Feed gas composition: | | | |
| Ethylene (vol. %) | 20.5 | 20.5 | 20.5 |
| Oxygen (vol. %) | 6.1 | 6.1 | 6.1 |
| $CO_2$ (vol. %) | 5.0 | 5.0 | 5.0 |
| NO (vol. ppm) | 10.1 | 10.1 | 10.1 |
| Vinyl chloride (vol. ppm) | 4.7 | 4.7 | 4.7 |
| Nitrogen | balance | balance | balance |
| 1 Week after at 230° C.: | | | |
| Conversion of ethylene (%) | 8.0 | 7.4 | 5.8 |
| Selectivity coefficient for ethylene oxide (%) | 86.8 | 87.7 | 89.1 |

TABLE 5-continued

| Remarks | stable | stable | stable |
|---|---|---|---|
| | Ex. 13 | Comp. Ex. 8 | Comp. Ex. 9 |
| Catalyst No. | 22 | 23 | 24 |
| Catalyst composition: | | | |
| Silver content (wt. %) | 7.2 | 7.2 | 7.2 |
| Rb/Ag (by atomic ratio) | 6.5/1000 | 1.5/1000 | 8.0/1000 |
| Feed gas composition: | | | |
| Ethylene (vol. %) | 20.5 | 20.5 | 20.5 |
| Oxygen (vol. %) | 6.1 | 6.1 | 6.1 |
| $CO_2$ (vol. %) | 5.0 | 5.0 | 5.0 |
| NO (vol. ppm) | 10.1 | 10.1 | 10.1 |
| Vinyl chloride (vol. ppm) | 4.7 | 4.7 | 4.7 |
| Nitrogen | balance | balance | balance |
| 1 Week after at 230° C.: | | | |
| Conversion of ethylene (%) | 4.1 | 4.8 | 0.8 |
| Selectivity coefficient for ethylene oxide (%) | 89.8 | 79.6 | 89.1 |
| Remarks | stable | stable | gradual activity drop |

EXAMPLE 14

Catalyst No. 25 was prepared in the following manner.

Dissolved in 24.3 g of water were 12.75 g of isopropylamine and 4.04 g of morpholine, followed by further dissolution of 15.73 g of silver nitrate and 0.067 g of rubidium nitrate in the resultant solution to prepare a dipping solution. Forty grams of a carrier, which had a specific surface area of 0.46 m$^2$/g, apparent porosity of 61.8% and pores, about 90% of said pores ranging from 1 to 30 micrometers, and contained about 99.5% of Al$_2$O$_3$, were immersed. The carrier with the dipping solution contained therein was dried at 145° C. for 3 hours, followed by its firing at 160° C. for 2 hours and at 260° C. for further 3 hours in air. As a result of analysis, this catalyst contained 8.5% of silver with Rb/Ag=5.8/1000 (by atomic ratio).

Using Catalyst No. 25, a reaction was conducted in exactly the same manner as in Example 1 except that the composition of the feed gas was slightly different. Results are given in Table 6.

EXAMPLE 15

Catalyst No. 26 was obtained in exactly the same manner as in Example 11 except for use of a carrier, which had a specific surface area of 0.74 m$^2$/g, apparent porosity of 53% and pores, about 88% of said pores ranging from 1 to 30 micrometers, and contained about 96.0% of Al$_2$O$_3$ and addition of rubidium nitrate in a different amount. As a result of analysis, Catalyst No. 26 contained 7.9% of silver with Rb/Ag=4.8/1000 (by atomic ratio).

Using Catalyst No. 26, a reaction was conducted in exactly the same manner as in Example 11. Results are given in Table 6.

COMPARATIVE EXAMPLE 10

Catalyst No. 27 was obtained in exactly the same manner as in Example 14 except for use of a carrier, which had a specific surface area of 1.03 m$^2$/g, apparent porosity of 53% and pores, about 65% of said pores ranging from 1 to 30 micrometers, and contained about 99.6% of Al$_2$O$_3$. As a result of analysis, Catalyst No. 27 contained 6.2% of silver with Rb/Ag=5.9/1000 (by atomic ratio).

Using Catalyst No. 27, a reaction was conducted in exactly the same manner as in Example 14. Results are given in Table 6.

It is readily envisaged from Examples 14 and 15 and Comparative Example 10 that good results are available where the specific surface area of the carrier of a catalyst is 0.8 m$^2$/g or smaller.

TABLE 6

| Catalyst No. | Ex. 14 25 | Ex. 15 26 | Comp. Ex. 10 27 |
|---|---|---|---|
| Specific surface area of carrier (m$^2$/g) | 0.46 | 0.74 | 1.03 |
| Catalyst composition: | | | |
| Silver content (wt. %) | 8.5 | 7.9 | 6.2 |
| Rb/Ag (by atomic ratio) | 5.9/1000 | 4.2/1000 | 5.9/1000 |
| Feed gas composition: | | | |
| Ethylene (vol. %) | 20.4 | 20.4 | 20.4 |
| Oxygen (vol. %) | 6.2 | 6.2 | 6.2 |
| $CO_2$ (vol. %) | 5.1 | 5.1 | 5.1 |
| NO (vol. ppm) | 10.2 | 10.2 | 10.2 |
| VCM (vol. ppm) | 4.7 | 4.7 | 4.7 |
| Nitrogen | balance | balance | balance |
| 1 Week after at 230° C.: | | | |
| Conversion of ethylene (%) | 5.3 | 4.2 | 1.7 |
| Selectivity coefficient for ethylene oxide (%) | 84.7 | 84.0 | 80.1 |
| 1 Week after at 250° C.: | | | |
| Conversion of ethylene (%) | 9.7 | 8.0 | <0.5 |
| Selectivity coefficient for ethylene oxide (%) | 80.1 | 79.4 | —* |
| | stable | stable | almost deactivated |

*Calculation was infeasible due to poor accuracy of the analysis.

EXAMPLE 16 AND COMPARATIVE EXAMPLES 11 & 12

In exactly the same manner as in Example 1, Catalyst Nos. 28, 29 and 30 were prepared. Using these catalysts, Catalyst Nos. 28, 29 and 30, reactions were carried out at 230° C. for 1 week with a feed gas the composition of which is given in Table 7. Results are shown in Table 7.

Then, further reactions were carried out at 230° C. for 1 week with another feed gas the composition of which is shown in Table 8. Results are also shown in Table 8.

From Example 16 and Comparative Examples 11 & 12, it is apparent that in each feed gas, the lower limit for the total concentration of a nitrogen oxide and/or nitrogen oxide precursor is about 1 vol. ppm and the lower limit for a chlorine-containing burning reaction decelerator is about 0.5 vol. ppm.

It is also clear from Example 1 and Comparative Examples 3, 4, 5 and 6 that high activities and high selectivity can be stably maintained only when a principal alkali metal contained in a catalyst is rubidium. It is also apparent from Examples 1–16 that the atomic ratio of rubidium to silver (Rb/Ag) is preferably 2/1000–7/1000 or most preferably 3/1000–6/1000.

TABLE 7

| Catalyst No. | Ex. 16 28 | Comp. Ex. 11 29 | Comp. Ex. 12 30 |
|---|---|---|---|
| Catalyst composition: | | | |
| Silver content (wt. %) | 8.3 | 8.3 | 8.3 |
| Rb/Ag (by atomic ratio) | 4.2/1000 | 4.2/1000 | 4.2/1000 |
| Feed gas composition: | | | |
| Ethylene (vol. %) | 20.8 | 20.8 | 20.8 |
| Oxygen (vol. %) | 6.2 | 6.2 | 6.2 |
| $CO_2$ (vol. %) | 5.1 | 5.1 | 5.1 |

TABLE 7-continued

| Catalyst No. | Ex. 16 28 | Comp. Ex. 11 29 | Comp. Ex. 12 30 |
| --- | --- | --- | --- |
| NO (vol. ppm) | 9.7 | 9.7 | 9.7 |
| Vinyl chloride (vol. ppm) | 4.8 | 4.8 | 4.8 |
| Nitrogen | balance | balance | balance |
| 1 Week after at 230° C.: | | | |
| Conversion of ethylene (%) | 8.1 | 8.0 | 8.1 |
| Selectivity coefficient for ethylene oxide (%) | 89.4 | 89.4 | 89.5 |
| Remarks | stable | stable | stable |

TABLE 8

| Catalyst No. | Ex. 16 28 | Comp. Ex. 11 29 | Comp. Ex. 12 30 |
| --- | --- | --- | --- |
| Feed gas composition: | | | |
| Ethylene (vol. %) | 20.3 | 20.6 | 20.5 |
| Oxygen (vol. %) | 6.1 | 6.0 | 6.2 |
| $CO_2$ (vol. %) | 1.4 | 1.5 | 1.5 |
| NO (vol. ppm) | 1.2 | 0.5 | 1.2 |
| Ethylene dichloride (vol. ppm) | 0.6 | 0.6 | 0.2 |
| Nitrogen | balance | balance | balance |
| 1 Week after at 230° C.: | | | |
| Conversion of ethylene (%) | 8.7 | 5.3 | 6.2 |
| Selectivity coefficient for ethylene oxide (%) | 88.6 | 88.0 | 84.3 |
| Remarks | stably performed. | conversion and selectivity coefficient both gradually dropped. | |

EXAMPLE 17 AND COMPARATIVE EXAMPLES 13–15

Using Catalyst Nos. 1, 7, 8 and 9, reactions were carried out under an elevated pressure of 15 kg/cm²G. Thirty gram portions of the catalysts were respectively packed in tubular reactors having an inner diameter of 17 mm and made of stainless steel, to each of which a feed gas consisting of 21.3 vol. % of ethylene, 6.2 vol. % of oxygen, 4.9 vol. % of carbon dioxide, 10.1 vol. ppm of nitrogen monoxide, 4.7 vol. ppm of vinyl chloride and the remainder of nitrogen was supplied at a space velocity of 2500 $H_v^{-1}$ and 15 kg/cm²G (converted under N.T.P.). The reaction was continued at 240° C. for 2 weeks. Results are summarized in Table 9.

TABLE 9

| Ex. No. | Cat. No. | Type of added alkali metal | Catalyst composition | | Conversion of ethylene (%) | Selectivity for ethylene oxide (%) | Remarks |
| --- | --- | --- | --- | --- | --- | --- | --- |
| | | | Ag content (%) | Me*/Ag atomic ratio | | | |
| Ex. 17 | 1 | $RbNO_3$ | 8.3 | 4.2/1000 | 7.1 | 85.0 | stable |
| Comp. Ex. 13 | 7 | $NaNO_3$ | 8.3 | 18/1000 | 0 | — | no catalytic activity |
| Comp. Ex. 14 | 8 | $KNO_3$ | 8.3 | 6/1000 | 0 | — | no catalytic activity |
| Comp. Ex. 15 | 9 | $CsNO_3$ | 8.3 | 2.2/1000 | 6.5 | 78.1 | stable |

*Me means an alkali metal.

In the experiment conducted at the elevated pressure of 15 kg/cm²G by using the feed gas which contained 4.9 vol. % of carbon dioxide, the silver catalyst containing sodium or potassium did not show any catalytic activity for the oxidation reaction of ethylene. On the other hand, the cesium-containing silver catalyst resulted in the low selectivity coefficient. Different from such catalysts, the rubidium-containing catalyst showed the high selectivity coefficient for ethylene oxide and was also stable. As demonstrated in the above experiment, only rubidium-containing silver catalysts show high selectivity, enjoy long service life as catalysts and remain stable when used with gases employed in actual plants for ethylene oxide, i.e., having a reaction pressure of 15 kg/cm²G and containing $CO_2$ at a level of about 5% or so.

COMPARATIVE EXAMPLES 16 & 17

Catalyst Nos. 31 and 32 were each prepared in exactly the same manner as in Example 1 except that as an additional alkali metal, a predetermined amount of sodium nitrate or potassium nitrate was added besides 0.067 g of rubidium nitrate.

Using Catalyst Nos. 31 and 32, reactions were respectively carried out under exactly the same conditions as those employed in the experiment conducted under the elevated pressure of 15 kg/cm²G in Example 17. Results shown in Table 10 were obtained.

TABLE 10

| Comp. Ex. | Catalyst composition | | Conversion of ethylene | Selectivity coefficient for ethylene oxide | Remarks |
| --- | --- | --- | --- | --- | --- |
| | Ag content | Alkali metal | | | |
| 16 | 8.3% | Na 200 ppm + Rb 280 ppm (Na/Ag = 11.3/1000 + Rb/Ag = 4.2/1000) | 0 | — | no catalytic activity |
| 17 | 8.3% | K 200 ppm + Rb 280 ppm (K/Ag = 6.6/1000 + Rb/Ag = 4.2/1000) | 0 | — | no catalytic activity |

Catalysts containing sodium or potassium as a principal active component and added with rubidium as disclosed in Japanese Patent Laid-open No. 115306/1979 do not show catalytic activities when applied at an elevated pressure of 15 kg/cm²G for gases containing about 5% of $CO_2$.

What is claimed is:

1. A process for preparing ethylene oxide which comprises contacting a feed gas comprising a mixture of ethylene, oxygen, from 1 to 20 vol. % of carbon dioxide, from 0.5 to 100 vol. ppm of a chlorine-containing reaction modifier and from 1 to 500 vol. ppm, calculated as nitrogen monoxide, of a nitrogen oxide and/or precursor thereof, with a catalyst consisting essentially of from 3 to 20 wt. % of silver and, as the only alkali metal, rubidium deposited on a porous fire-resistant carrier, said carrier having a specific surface area of from 0.05 to 1.0 m$^2$/g, the atomic ratio of said rubidium to said silver (Rb/Ag) being from 2/1000 to 7/1000.

2. A process as claimed in claim 1, wherein the specific surface area of the porous fire-resistant carrier is in the range of 0.1-0.5 m$^2$/g.

3. A process as claimed in claim 1, wherein the atomic ratio Rb/Ag is 3/1000-6/1000.

4. A process as claimed in claim 1, wherein the nitrogen oxide and/or nitrogen oxide precursor is contained in a total amount of 3-200 vol. ppm calculated in terms of nitrogen monoxide.

5. A process as claimed in claim 1, wherein the chlorine-containing reaction modifier is contained in an amount of 1.0-50.0 vol. ppm.

6. A process as claimed in claim 1, wherein the feed gas mixture contains 1-10 vol. % of carbon dioxide.

7. A process as claimed in claim 1, wherein the reaction temperature is 150°-300° C.

8. A process as claimed in claim 1, wherein the reaction pressure is 0-50 kg/cm$^2$.

9. A process as claimed in claim 1, wherein the catalyst contains from 5 to 12 wt. % of silver.

10. The process as claimed in claim 1, wherein said chlorine-containing reaction modifier is selected from the group consisting of vinyl chloride, ethylene dichloride, methyl chloride, chlorobenzene and diphenyl chloride.

11. A process as claimed in claim 1, wherein said nitrogen oxide is NO, $NO_2$, $N_2O_4$, $N_2O_5$ or $N_2O_3$, and said nitrogen oxide precursor is selected from the group consisting of methylamine, ethylamine, n-propylamine, iso-propylamine, ethanolamine, ethylenediamine, and ammonia.

12. A process as claimed in claim 1, wherein said porous fire-resistant carrier is selected from the group consisting of alumina, silica, magnesia, zirconia, silicon carbide and diatomaceous earth.

13. A process as claimed in claim 1, wherein said carrier has an apparent porosity of from 40 to 60 vol. % and said carrier has pores, at least 70% of which have pore diameters ranging from 1.5 to 15.0 microns.

* * * * *